(12) United States Patent
Wall et al.

(10) Patent No.: US 10,117,975 B2
(45) Date of Patent: Nov. 6, 2018

(54) MULTI-MODAL WOUND TREATMENT APPARATUS

(71) Applicant: INTEGRATED HEALING TECHNOLOGIES, Franklin, TN (US)

(72) Inventors: Billy Wall, Arrington, TN (US); Stephen Galbraith, Franklin, TN (US); Robert Porter, Franklin, TN (US)

(73) Assignee: Integrated Healing Technologies, LLC, Franklin, TN (US)

( * ) Notice: Subject to any disclaimer, the term of this patent is extended or adjusted under 35 U.S.C. 154(b) by 0 days.

(21) Appl. No.: 14/378,306

(22) PCT Filed: Feb. 13, 2013

(86) PCT No.: PCT/US2013/025901
§ 371 (c)(1),
(2) Date: Aug. 12, 2014

(87) PCT Pub. No.: WO2013/123022
PCT Pub. Date: Aug. 22, 2013

(65) Prior Publication Data
US 2015/0290364 A1 Oct. 15, 2015

Related U.S. Application Data

(60) Provisional application No. 61/633,515, filed on Feb. 13, 2012, provisional application No. 61/633,516, (Continued)

(51) Int. Cl.
*A61M 1/00* (2006.01)
*A61F 13/00* (2006.01)
(Continued)

(52) U.S. Cl.
CPC ..... *A61M 1/0031* (2013.01); *A61F 13/00068* (2013.01); *A61L 2/202* (2013.01);
(Continued)

(58) Field of Classification Search
CPC .............. A61M 1/0023; A61M 1/0025; A61M 1/0027; A61M 1/0029; A61M 1/0031;
(Continued)

(56) References Cited

U.S. PATENT DOCUMENTS 4,218,610 A * 8/1980 Baxter, Jr. ......... G01N 15/1227
377/12
5,069,880 A * 12/1991 Karlson ................. A61L 2/202
422/186.07
(Continued)

FOREIGN PATENT DOCUMENTS

EP 1100574 A1 5/2001
KR 101123897 B1 4/2012
(Continued)

OTHER PUBLICATIONS

International Search Report and Opinion dated May 6, 2013, Commissioner for Patents.
(Continued)

*Primary Examiner* — Andrew Gilbert
*Assistant Examiner* — James D Ponton
(74) *Attorney, Agent, or Firm* — Patterson Intellectual Property Law, PC; Hilary Dorr Lang

(57) ABSTRACT

The wound treatment apparatus combines an internal negative pressure (vacuum) pump and an internal positive pressure (compressor) pump connectable to an external oxygen supply for providing both negative pressure wound therapy and hyperbaric oxygen wound therapy to a wound site. The apparatus also includes a user interface operatively connected to an electronic controller that monitors and actuates the vacuum and compressor pumps. The user interface and controller enables the apparatus to provide multiple modes
(Continued)

of operation and the ability to selectively change between negative pressure therapy operational modes and hyperbaric oxygen operational modes.

18 Claims, 6 Drawing Sheets

Related U.S. Application Data filed on Feb. 13, 2012, provisional application No. 61/633,517, filed on Feb. 13, 2012, provisional application No. 61/633,527, filed on Feb. 13, 2012, provisional application No. 61/633,528, filed on Feb. 13, 2012, provisional application No. 61/633,529, filed on Feb. 13, 2012.

(51) Int. Cl.
*A61L 2/20* (2006.01)
*A61M 35/00* (2006.01)

(52) U.S. Cl.
CPC .......... *A61M 1/009* (2014.02); *A61M 1/0084* (2013.01); *A61M 1/0088* (2013.01); *A61M 35/00* (2013.01); *A61F 2013/0028* (2013.01); *A61M 1/0037* (2013.01); *A61M 2202/0208* (2013.01); *A61M 2205/05* (2013.01); *A61M 2205/3331* (2013.01); *A61M 2209/10* (2013.01); *A61M 2230/00* (2013.01)

(58) Field of Classification Search
CPC .............. A61M 1/0035; A61M 1/0066; A61M 1/0084; A61M 27/00; A61F 13/00068; A61F 13/0216
See application file for complete search history.

(56) References Cited

U.S. PATENT DOCUMENTS

| | | | |
|---|---|---|---|
| 7,524,315 B2* | 4/2009 | Blott | A61M 1/0001 604/317 |
| 8,021,348 B2* | 9/2011 | Risk, Jr. | A61M 1/0058 604/305 |
| 8,100,956 B2* | 1/2012 | Quisenberry | A61F 7/02 602/2 |
| 2007/0118096 A1 | 5/2007 | Smith et al. | |
| 2007/0260226 A1* | 11/2007 | Jaeb | A61M 1/0005 604/543 |
| 2008/0071330 A1 | 3/2008 | Quisenberry et al. | |
| 2008/0140029 A1 | 6/2008 | Smith et al. | |
| 2008/0250564 A1* | 10/2008 | Stryker | A61G 7/001 5/615 |
| 2009/0293879 A1* | 12/2009 | Franberg | A61M 16/10 128/205.27 |
| 2010/0030132 A1* | 2/2010 | Niezgoda | A61L 2/035 604/22 |
| 2010/0150991 A1 | 6/2010 | Bernstein | |
| 2011/0275983 A1 | 11/2011 | Quisenberry et al. | |

FOREIGN PATENT DOCUMENTS

| | | |
|---|---|---|
| WO | 2006119473 A2 | 11/2006 |
| WO | 2007062024 A1 | 5/2007 |
| WO | 2008130689 | 10/2008 |

OTHER PUBLICATIONS

Notice of Opposition of corresponding European patent application No. 13749574.3, dated Oct. 11, 2017, 30 pages.
Response to Notice of Opposition of European patent application No. 13749574.3, dated Jun. 4, 2018, 6 pages.

* cited by examiner

MULTI-MODAL WOUND TREATMENT APPARATUS

TECHNICAL FIELD

The present invention relates to methods and systems for providing therapeutic treatment of chronic and acute wounds. More particularly, the present invention pertains to devices and methods for delivering multi-modal treatment therapies to a wound site.

BACKGROUND ART

Chronic and acute wounds, including pressure ulcers, diabetic wounds, and burns, present significant challenges to the health care industry. Patient care providers are actively seeking methods, devices, and systems for treating such wounds at a lower cost and with greater efficacy.

Conventional treatments for chronic wounds typically include either negative pressure therapy and/or hyperbaric oxygen therapy.

Negative pressure therapy is the controlled application of sub-atmospheric pressure to a wound using a therapy unit, such as a vacuum or suction device, to expose the wound to negative pressure to help promote wound healing. The wound is typically covered to facilitate the application of negative pressure and suction at the wound area. Various types of resilient, open cell foam surface dressings are typically sealed within an adhesive drape to provide the sub-atmospheric pressure at the wound site. Exudates are drained from the wound site and typically directed to a canister that stores the fluids and/or infectious material until properly disposed. Negative pressure wound therapy is often prescribed for chronic and acute wound types such as diabetic wounds, pressure ulcers, abdominal wounds, trauma wounds, various burns, flaps and grafts. However, negative pressure therapy may be less effective on patients having vascular disorders, such as diabetes, because negative pressure therapy can create a hypoxic environment at the wound. In current hospital settings, portable vacuum pumps are often rented or purchased for the purpose of providing negative pressure therapy. This can significantly increase the cumulative costs of providing wound care.

Hyperbaric oxygen therapy is the controlled application of oxygen to a wound at greater-than-atmospheric pressures. Oxygen is typically required for all new cell growth. Chronic or non-healing wounds tend to exhibit low oxygen tensions, or tend to be ischemic. A wound can become dormant if the amount of poorly oxygenated wound tissue reaches a critical mass. In this state, the body may no longer recognize the need to heal the affected area, thereby exacerbating the lack of oxygen in the wound and impairing healing of the wound by the body. Oxygen therapy is particularly useful for patients with poor circulation. The oxygen helps to kill bacteria and when applied to an open wound at a hyperbaric level, the oxygen is dissolved into the wound and absorbed by the surface wound tissue. The cells of the wound tissue that absorb the oxygen will begin metabolic activity in response to the increased oxygen tension. When the oxygen source is removed, the previously active cells request more oxygen from the body. The body responds by beginning to form new blood cells, and thus, starting the healing process. Accordingly, when delivered to a wound site under hyperbaric conditions, oxygen may act as a primary wound treatment fluid Typically, hyperbaric oxygen therapy is delivered by placing the patient in a hyperbaric chamber that encompasses the full body of the patient or an entire extremity, such as a leg or an arm. Such chambers are problematic due to their lack of portability, the difficulty in sterilization of the chambers between patients, and the potential adverse effects of breathing oxygen at hyperbaric pressure. Preferably, hyperbaric oxygen treatment should be localized at the wound site rather than applied to the patient's entire body or extremity.

While both negative pressure and hyperbaric oxygen therapies are each believed to be effective when administered as separate wound care treatments, many patients may benefit from a treatment protocol incorporating both negative pressure and hyperbaric oxygen therapies. Because existing hyperbaric oxygen treatment is typically performed in a hyperbaric chamber, switching between negative pressure therapy and hyperbaric oxygen therapy is time-consuming. Before entering a hyperbaric oxygen chamber, a patient must first be disconnected from the negative therapy device. Thee negative pressure therapy dressing, which typically includes packing materials, a drain, tubing, and sealing material, must then be removed. Following hyperbaric oxygen treatment, a new negative pressure dressing would have to be applied. These procedures are wasteful and time-consuming, making it difficult, if not impossible, to alternate between negative pressure therapy and hyperbaric oxygen therapy every few minutes or less.

More recently, wound care systems and methods have been developed that combine negative and positive pressure (e.g. hyperbaric oxygen) wound treatment therapies. Such methods and systems are described, for example, in U.S. Pat. No. 7,648,488 issued Jan. 19, 2010; U.S. Pat. No. 8,357,130 issued Jan. 22, 2013; U.S. Patent Publication No. 2008/0140029; and U.S. Patent Publication No. 2010/0121287; all of which are hereby incorporated in their entirety by reference.

Wound care treatment may be further enhanced by deactivating pathogenic microorganisms within the wound environment and physically removing the deactivated microorganisms and other toxins from the wound site. While antibiotics and other drugs may be effective in destroying bacteria and other pathogens, their activity may disrupt the cell walls of the microorganisms, thereby releasing harmful enzymes and other toxins into the wound environment. These harmful enzymes and toxins must be removed or they may become cytotoxic.

It is also known that when planktonic, free floating, individual microorganisms, like bacteria, attach to a surface and gather in groups within a wound environment, they may produce an extra-cellular matrix called a biofilm. Biofilms are held together and protected by a matrix of excreted polymeric compounds called EPS (exopolysacchride). Biofilms provide a protective environment for microorganisms that exist within the biofilm mass and a level of immunity from antibiotic treatments, except in doses that would be fatal to the patient. Consequently, biofilm microorganisms are not affected by the body's own infection-resistance mechanisms. In addition, bacterial biofilms may impair cutaneous wound healing and reduce topical antibacterial efficiency in healing or treating infected skin wounds.

Hypochlorous acid (HOCl) is an active component found in the human immune system as a natural defense against infection, and thus kills bacteria, fungi and viruses without creating mechanisms for drug resistance. Hypochlorous acid compounds can be a safe, fast acting, broad spectrum antimicrobial for topical application, effective against all groups of hydrophobic, hydrophilic, gram-negative and gram-positive bacteria, and yeast, including *pseudomonas*

*aeruginosa, Staphylococcus aureus,* and multi-drug resistant organisms like methicillin resistant *staphylococcus aureus* (MRSA), and vancomycin resistant enterococci (VRE). In addition, hypochlorous acid compounds rapidly penetrate and disrupt biofilm and eradicate the pathogens, the major factor that inhibits wound healing. Unlike most antibiotics, which can take many hours to work, hypochlorous acid compounds, even at small doses, can help eradicate bacteria, fungi and viruses in minutes. When applied topically within a wound environment, hypochlorous acid compounds immediately disrupt and eradicate the bio-film, which surrounds and deactivates a broad spectrum of pathogenic microorganisms. Hypochlorous acid generally controls the tissue bacterial bio-burden without inhibiting the wound healing process and is also commonly associated with improved wound closure. Accordingly, a wound treatment therapy using a stabilized hypochlorous acid compound has recently been disclosed in U.S. Patent Publication No. 2012/0328680, the entirety of which is hereby incorporated by reference.

What is needed, then, is an apparatus that can effectively, and at low cost, operate in multiple treatment modes to deliver one or more different wound therapies to a wound site.

DISCLOSURE OF THE INVENTION

In various embodiments, the wound treatment apparatus of the present invention may provide, using a unitary portable device, both negative pressure wound therapy and positive pressure (hyperbaric oxygen) wound therapy to a wound site.

In one embodiment of the invention, the wound treatment apparatus includes a portable housing with a carry handle. A wound exudate container may be supported on the housing. A positive pressure device, e.g., a compressor pump, is disposed within the housing and is configured so that it can be fluidly coupled to an external source of oxygen and to an external wound dressing. The compressor pump delivers therapeutically effective levels of hyperbaric oxygen as a primary wound treatment fluid to the wound dressing during a first wound treatment mode. A negative pressure device, e.g. a vacuum pump, is also disposed within the housing and is configured for fluid coupling to the external wound dressing. The vacuum pump creates therapeutically effective levels of negative pressure to the wound dressing during a second wound treatment mode. A controller is disposed within the housing and operatively connected to the compressor pump and to the vacuum pump. A user interface is provided on the housing to communicate with the controller. The controller switches the apparatus between the first wound treatment mode and the second wound treatment mode. An oxygen concentrator may also be disposed within the housing and operatively coupled to the compressor pump so that the oxygen concentrator may supply oxygen enriched air to the compressor pump.

In some embodiments of the invention, oxygen and vacuum accumulator valves may be operatively coupled to the controller. An oxygen accumulator may be fluidly coupled to the compressor pump via the oxygen accumulator valve. A vacuum accumulator may be fluidly coupled to the vacuum pump via the vacuum accumulator valve. In such embodiments, the controller may be further configured to selectively actuate the oxygen and vacuum accumulator valves to facilitate application of positive and negative pressures at the wound dressing when the apparatus is transitioning between the first and second wound treatment modes.

According to another aspect of the invention, the apparatus may include a supplemental fluid delivery system in the housing, including at least one supplemental fluid vial adapted to contain a supplemental wound treatment fluid, such as an antiseptic, a medication, or hypochlorous acid. In such embodiments, the controller may be further configured to cause the supplemental fluid delivery system to deliver the supplemental wound treatment fluid to the wound dressing during the first wound treatment mode.

In a further aspect, the apparatus of the present invention may have a self-sterilization system, e.g., an ozone generator disposed within the housing. The self-sterilization system is responsive to the controller to selectively circulate sterilizing fluid, e.g. ozone, through the compressor pump and vacuum pump during a self-sterilization mode.

According to yet another aspect of the invention, an exudate safety system may be disposed within the housing. The exudate safety system may include a first pressure sensor to measure fluid pressures inside a wound treatment fluid output line, a second pressure sensor to measure fluid pressures inside a vacuum return line, and logic unit responsive to the first and second pressure sensors to determine and indicate exudate contamination of the apparatus.

Some embodiments of the apparatus may include a blood detection system disposed within the housing. The blood detection system includes at least one blood detection sensor that is functional to detect blood in exudate drawn from the wound dressing during the second wound treatment mode.

The above described features and advantages, as well as others, will become more readily apparent to those of ordinary skill in the art by reference to the following detailed description and accompanying drawings.

BRIEF DESCRIPTION OF THE DRAWINGS

The present invention may take form in various system and method components and arrangement of system and method components. The drawings are only for purposes of illustrating exemplary embodiments and are not to be construed as limiting the invention. The drawings illustrate the present invention, in which.

BEST MODE FOR CARRYING OUT THE INVENTION

Figure 1:
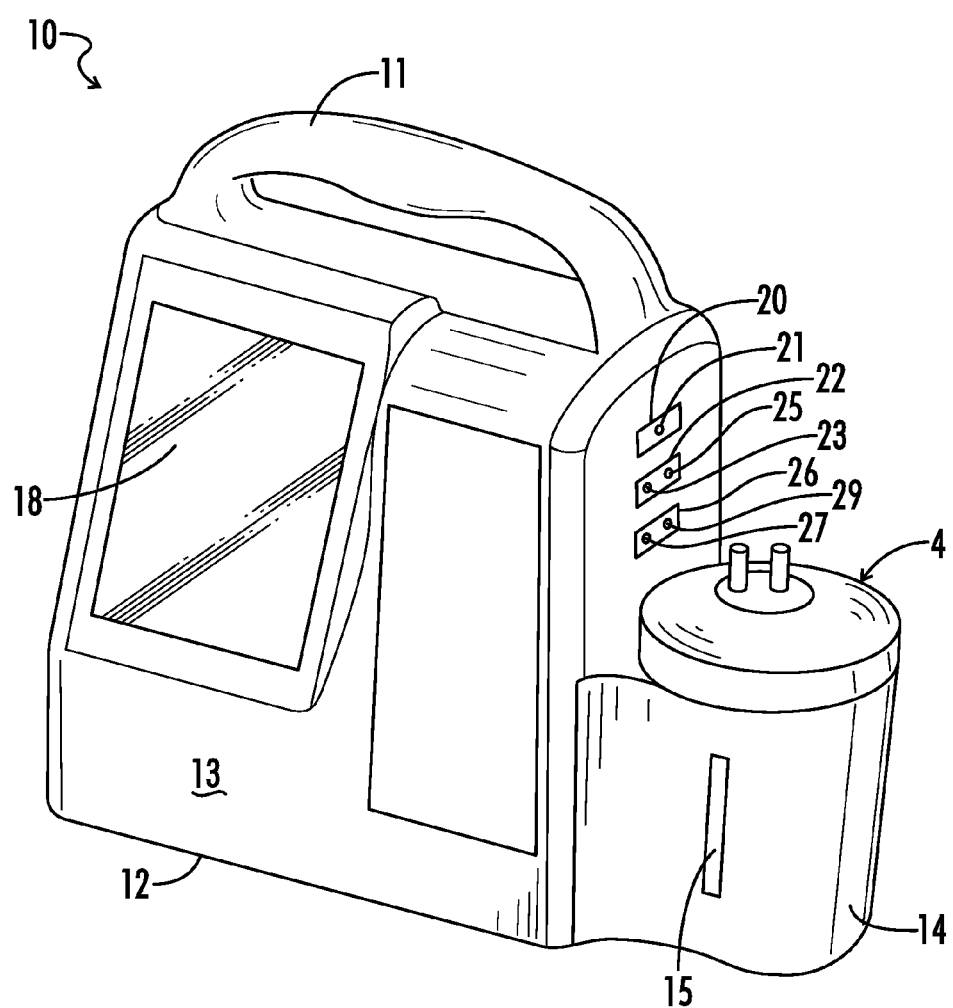
FIG. 1 is a perspective view of an embodiment of the apparatus of this invention.

Referring now to the drawings, FIGS. 1-8 illustrate an embodiment of the wound treatment apparatus of the present invention, which is designated generally as reference numeral 10. In an embodiment, wound treatment apparatus 10 is configured to provide both negative pressure wound treatment and positive pressure (e.g., hyperbaric oxygen) wound treatment to a wound site. The wound site may be covered by a wound dressing 6 (FIG. 2) that hermetically seals the wound site and facilitates the wound treatment. For example, the negative pressure and hyperbaric oxygen therapies may be delivered at therapeutic levels via a wound dressing using one or more operational modes.

Therapeutically effective levels of hyperbaric oxygen and negative pressure treatments may be affected by different combinations of fluid pressures, fluid concentrations, fluid flow rates, treatment durations, and treatment intervals, as is known in the art. For example, in some embodiments of the present invention, therapeutically effective wound treatment levels and wound treatment protocols can be determined generally in accordance with the methods and principles and described in U.S. Pat. Nos. 7,648,488, 8,357,130, U.S. Patent Publication No. 2008/0140029, and U.S. Patent Publication No. 2010/0121287, all of which are hereby incorporated in their entirety by reference.

An example of a wound treatment protocol combining the application of negative pressure and hyperbaric oxygen treatments can include administering hyperbaric oxygen therapy to the wound in a range of approximately 8 minutes to approximately 12 minutes and administering negative pressure therapy to the wound at less than 1 atmosphere for approximately 8 minutes to approximately 12 minutes. However, the wound treatment cycle times and ranges may vary according to the nature and severity of the wound being treated and according to the wound response to the treatment. The hyperbaric oxygen therapy and the negative pressure therapy are administered intermittently such that negative pressure therapy is administered immediately following the administration of hyperbaric oxygen therapy and hyperbaric oxygen therapy is administered immediately following the administration of negative pressure therapy. In this exemplar wound treatment protocol, the wound may be subject to an absolute pressure of from approximately 60 mmHg to approximately 160 mmHg during the administration of negative pressure therapy. Administering hyperbaric oxygen therapy may include supplying oxygen or humidified oxygen to the wound at a flow rate of approximately 0.1 liters per minute to approximately 3 liters per minute.

As shown in FIG. 1, an embodiment of the wound treatment apparatus 10 of the present invention may include a main unit body or housing 12 including a housing wall 13 that supports and encloses a variety of internal components within the device interior. The housing 12 is preferably provided with exterior dimensions and geometry to facilitate portability of the apparatus 10, including for example an integral or attached carrying handle 11. Housing 12 may further include a user interface 18 integrated in, or attached to the exterior wall 13 of the housing 12. The interface 18 allows a user of the apparatus to monitor and set the various operational modes of the apparatus. In some embodiments, the user interface 18 may be a resistive or capacitive touch screen display, as generally known in the art, further having a smooth flat screen that is easily cleaned. In other embodiments, the user interface 18 may combine an LCD or other visual display screen with one or more user input devices, such as a key pad, touch pad, joy stick, switches, buttons, and toggles.

In some embodiments, a side pocket 14 may be attached to or integrally formed with housing wall 13. Side pocket 14 is preferably configured to receive and support a removable exudate canister 4. Side pocket 14 may further include an open or translucent vertical slot 15 in a wall of the pocket 14 so that fluid levels in exudate canister 4 may be visually monitored. Additional support pockets may be formed in or attached to the exterior of housing 12 to hold containers of hypochlorous acid or other supplemental wound treatment fluids, as described in more detail below.

In its various modes of operation, wound treatment apparatus 10 may fluidly communicate with wound dressing 6 and/or with external wound treatment fluid sources. To enable and accommodate this functionality, housing 12 may also be provided with separate lumen connectors or connector panels 20, 22 and 26, the purposes of which will be described more particularly below.

Figure 2:
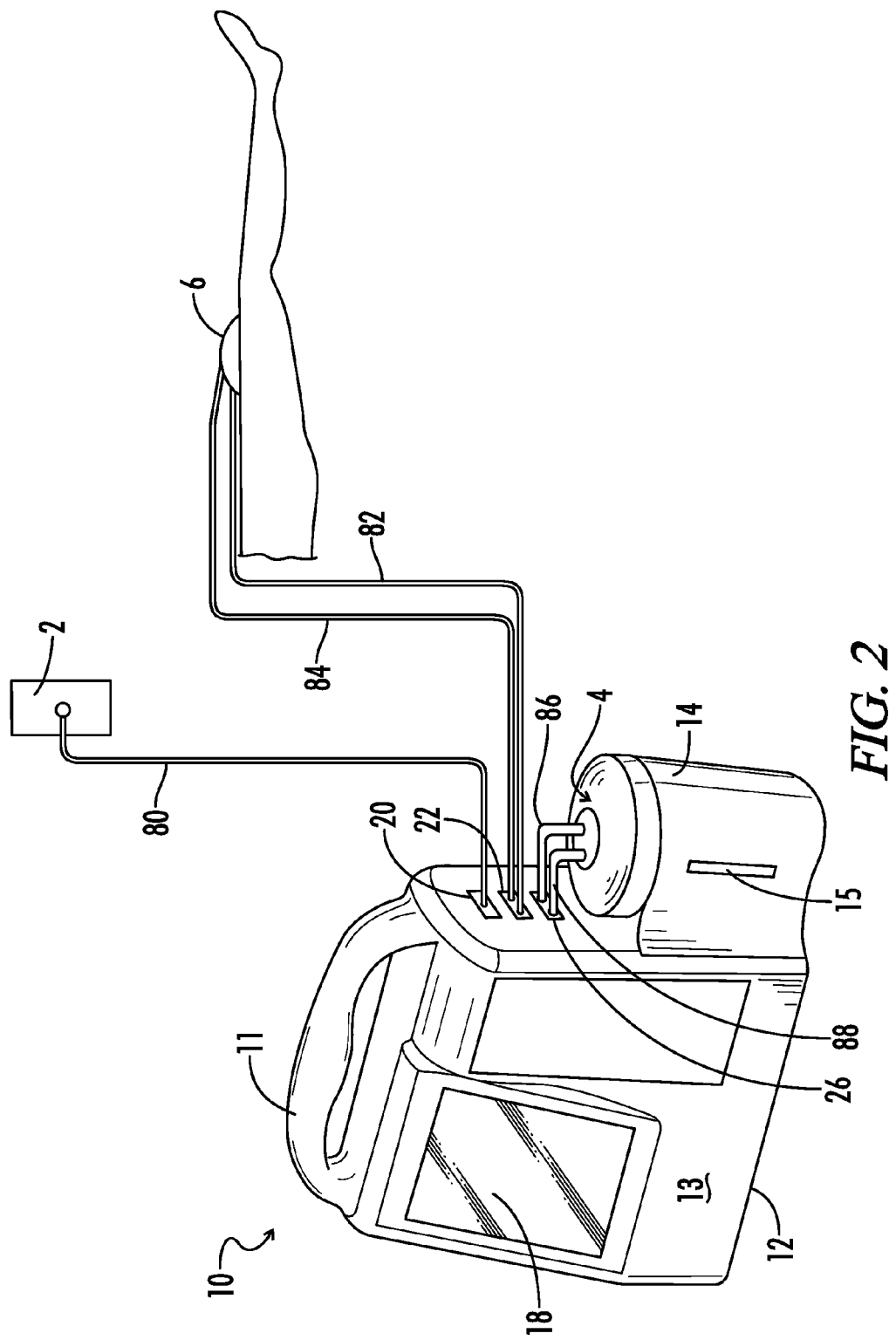
FIG. 2 is a perspective view of an embodiment of the apparatus connected to a wound dressing applied to a wound site and a removable exudate canister.

FIG. 2 shows apparatus 10 in a typical wound treatment application. In the embodiment as shown, various fluid transport lines or lumens 80, 82, 84, 86 and 88 respectively couple wound treatment apparatus 10 to an external source of a primary wound treatment fluid, e.g. oxygen supply source 2, to exudate canister 4, and to wound dressing 6.

In many embodiments and modes of operation, the external oxygen supply source 2 may be an external oxygen tank (not shown) or a wall-mounted oxygen port 2 connected to an in-house oxygen system.

Figure 3:
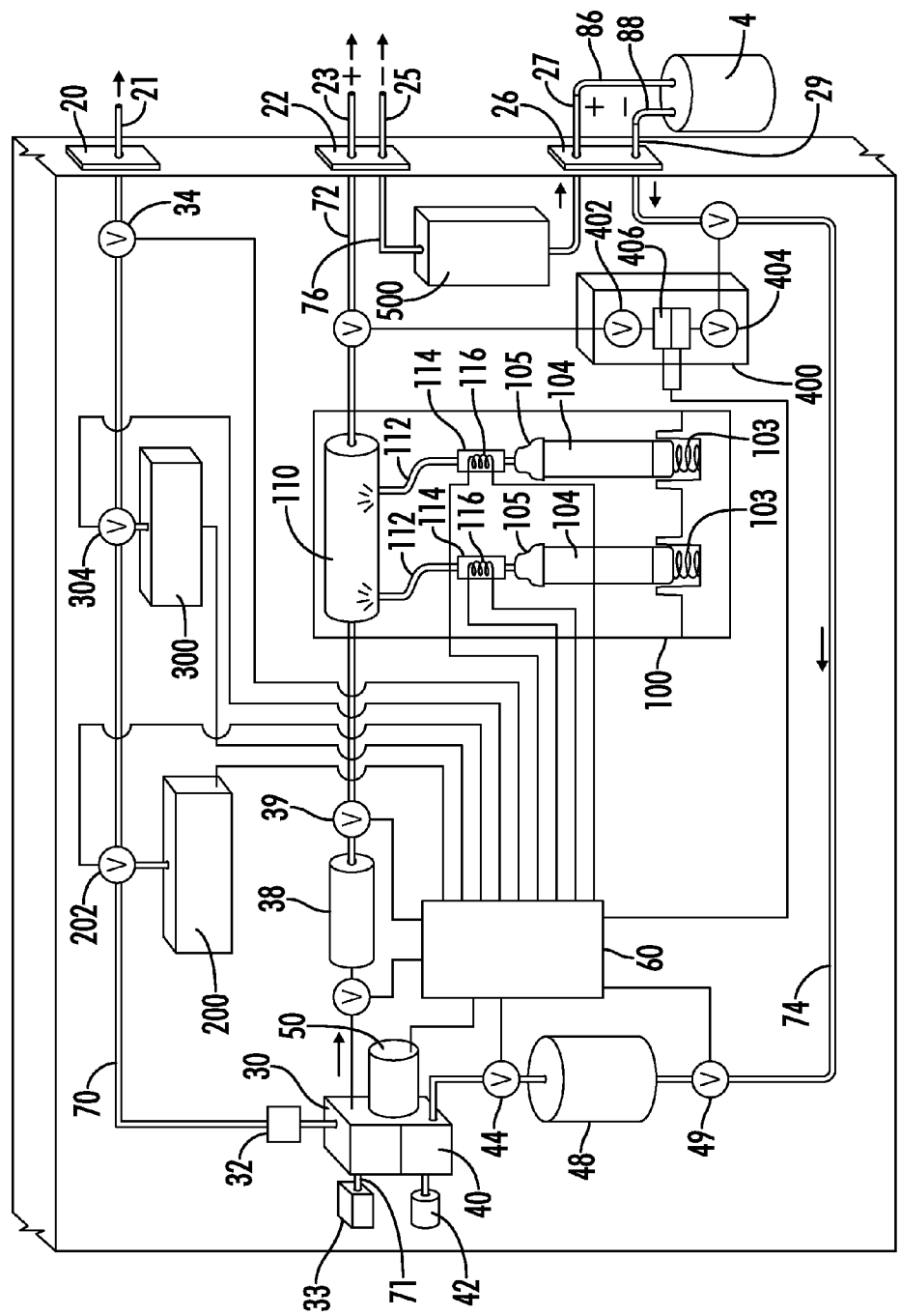
FIG. 3 is a simplified schematic of the internal components of the apparatus of FIG. 1.

Ideally, lumen connectors or connector panels 20, 22 and 26 each are attached to, formed in, or otherwise coupled to the housing wall 13 and have thru-wall fittings that are designed to ensure proper connection to their respective fluid lines or lumens 80, 82, 84, 86, and 88 between wound treatment apparatus 10 and oxygen source 2, exudate canister 4 and wound dressing 6. Thus, in the embodiment shown in FIGS. 2 and 3, oxygen supply connector 20 has a single oxygen supply fitting 21 (FIG. 3). An oxygen supply lumen 80 connects external oxygen supply 2 to oxygen supply fitting 21 of oxygen supply connector 20.

In the embodiment of FIGS. 2 and 3, wound treatment fluid connector 22 includes positive and negative pressure wound treatment fluid fittings 23 and 25. A positive pressure line or positive pressure wound treatment fluid lumen 82 connects wound dressing 6 to positive pressure wound treatment fluid fitting 23. A negative pressure line or negative pressure wound treatment fluid lumen 84 connects wound dressing 6 to negative pressure wound treatment fluid fitting 25.

As also shown in the embodiment of FIGS. 2 and 3, exudate connector 26 includes positive and negative pressure exudate fittings 27 and 29. Positive pressure exudate line or lumen 86 connects positive pressure exudate fitting 27 to removable exudate canister 4. Negative pressure exudate line or lumen 88 connects exudate canister 4 to negative pressure exudate fitting 29.

Referring now to FIG. 3, in some embodiments wound treatment apparatus 10 may include a negative pressure device and a positive pressure device configured inside housing 12. In some embodiments, the positive pressure device may be a compressor pump 30. The negative pressure device may be a vacuum pump 40.

In some embodiments, apparatus 10 may further include one or more of a supplemental fluid delivery system 100, an oxygen concentrator 200, a self-sterilization system 300, an exudate safety system 400, and a blood detection system 500, as further described below.

In some embodiments, compressor pump 30 may be of a conventional design suitable for use in medical applications, including being configured to provide a magnitude and duration of positive pressure at wound 6 that is effective for use in hyperbaric oxygen wound treatment. Vacuum pump 40 may also be of a conventional design suitable for medical applications, including being configured to provide a magnitude and duration of negative pressure that is effective for use in negative pressure wound treatment.

Each pump 30 and 40 may be driven independently by its own electrical motor or, as shown, separately driven by a single electric motor 50. As shown, the input side of compressor pump 30 may be fed by an oxygen source line 70 connected in fluid communication with oxygen supply fitting 21 and alternatively by an ambient air source line 71 that is in open communication to the atmosphere outside housing 18.

Oxygen source line 70 may include a filter 32 to keep dust and other particulates from entering compressor pump 30 from the external oxygen source 2. Ambient air source line 71 may include a filter 33 to keep dust and other particulates from entering compressor pump 30 from outside ambient air drawn into the compressor pump 30. Oxygen source line 70 may further include an oxygen source valve 34, which selectively opens and closes to control the supply of oxygen from external oxygen source 2.

The output side of compressor pump 30 may be connected to positive pressure wound treatment fluid fitting 23 of wound treatment fluid connector 22 by wound treatment fluid output line 72. Wound treatment fluid output line 72 may include a wound treatment fluid output valve 36 which selectively opens and closes to control the supply of oxygen under pressure to wound dressing 6.

In some embodiments, a vacuum return line 74 connects negative pressure exudate fitting 29 of exudate connector 26 to the intake side of vacuum pump 40. Vacuum return line 74 may further include a vacuum return valve 44, which selectively opens and closes to draw a vacuum pressure on the wound site through exudate canister 4. A drainage loop line 76 connects negative pressure wound treatment fluid fitting 25 of wound treatment fluid connector 22 to positive pressure exudate fitting 27 of exudate connector 26.

The outlet side of vacuum pump 40 may be connected to a filter/muffler 42, to dampen pump noise and/or inhibit the escape of exudate odors.

In an embodiment as shown in FIG. 3, compressor pump 30, vacuum pump 40, motor 50 and valves 36, 44, may be functionally coupled (by direct electrical wiring or other conventional electrical and/or fluid circuitry) to a logic unit or controller 60. In some embodiments, various conventional pressure and control sensors, relief valves, and control valves (not shown) may also be coupled to the controller 60 and to one or more of the illustrated fluid lines, components, and valves.

Wound treatment apparatus 10 may be electrically powered by any desirable means, such as an electrical AC grid connection or internal battery cells and power packs for portable convenience. Such power supplies are well known in the electrical arts and readily applied for use in medical device applications. In various embodiments, the controller 60 may have its own power supply or be connected to an internal apparatus power supply (not shown).

Controller 60 may be an electromechanical controller, a programmable logic controller, a microcontroller, a microprocessor, or other controller of conventional design, as is well know in the control arts. Controller 60 may be operatively connected to the user interface 18 to receive commands and/or to display information about the operation and status of the apparatus 10.

Controller 60 may be programmed or otherwise configured to monitor and control operation of the pumps, motor(s) and other active components in apparatus 10. In particular, controller 60 may be configured to cause apparatus 10 to selectively operate in various modes, including a first wound treatment mode (e.g. a positive pressure mode), a second wound treatment mode (e.g. a negative pressure mode), a transition mode, and a self-sterilization mode, as further described below.

In some embodiments when operating in a first wound treatment mode, or positive pressure mode, controller 60 actuates compressor pump 30 and opens valves 34 and 36 to draw oxygen from the external oxygen source 2. Actuation of compressor pump 30 further pushes oxygen into wound dressing 6 at a positive pressure above atmospheric pressure, via wound treatment fluid output line 72, positive pressure wound treatment fluid fitting 23, and wound treatment fluid supply lumen 82.

In some embodiments when operating in a second wound treatment mode, or a negative pressure mode, controller 60 activates vacuum pump 40 and opens valve 44 to draw a negative pressure within wound dressing 6 via negative pressure wound treatment lumen 84, negative pressure wound treatment fitting 25, and drainage loop line 76. This draws exudate from the wound site 6 into exudate canister 4 via positive pressure exudate fitting 27 and positive pressure exudate lumen 86.

In some embodiments, wound treatment apparatus 10 may operate in a temporary transition mode when changing between the positive pressure mode and the negative pressure mode. The transitional mode allows fluids in the various lines and lumens to quickly clear and for pressures, both negative and positive, to quickly build when switching between the positive and negative pressure modes.

Wound treatment fluid output line 72 may, in some embodiments, be fluidly coupled to compressor pump 30 through an oxygen accumulator system, including oxygen accumulator 38 and associated oxygen accumulator valve 39. Vacuum return line 74 may be fluidly coupled to vacuum pump 40 via a vacuum accumulator system including vacuum accumulator 48 and an associated vacuum accumulator valve 49. Oxygen accumulator 38 stores a volume of oxygen under a positive pressure, while vacuum accumulator 48 maintains its volume under a negative pressure. The accumulation of positive and negative pressures may be used to help expedite, e.g. accelerate, the pressurization of wound dressing 6, both positively and negatively, when transitioning between the negative and positive pressure modes. Accumulators 38 and 48 may each have various pressure sensors (not shown) and relief valves (not shown) that are operatively coupled to controller 60, which monitors and controls the pressure levels of the accumulators. Similarly, valves 39 and 49 are also coupled to controller 60, which is configured to control the actuation of both valves.

Supplemental Fluid Delivery System

Figure 4:
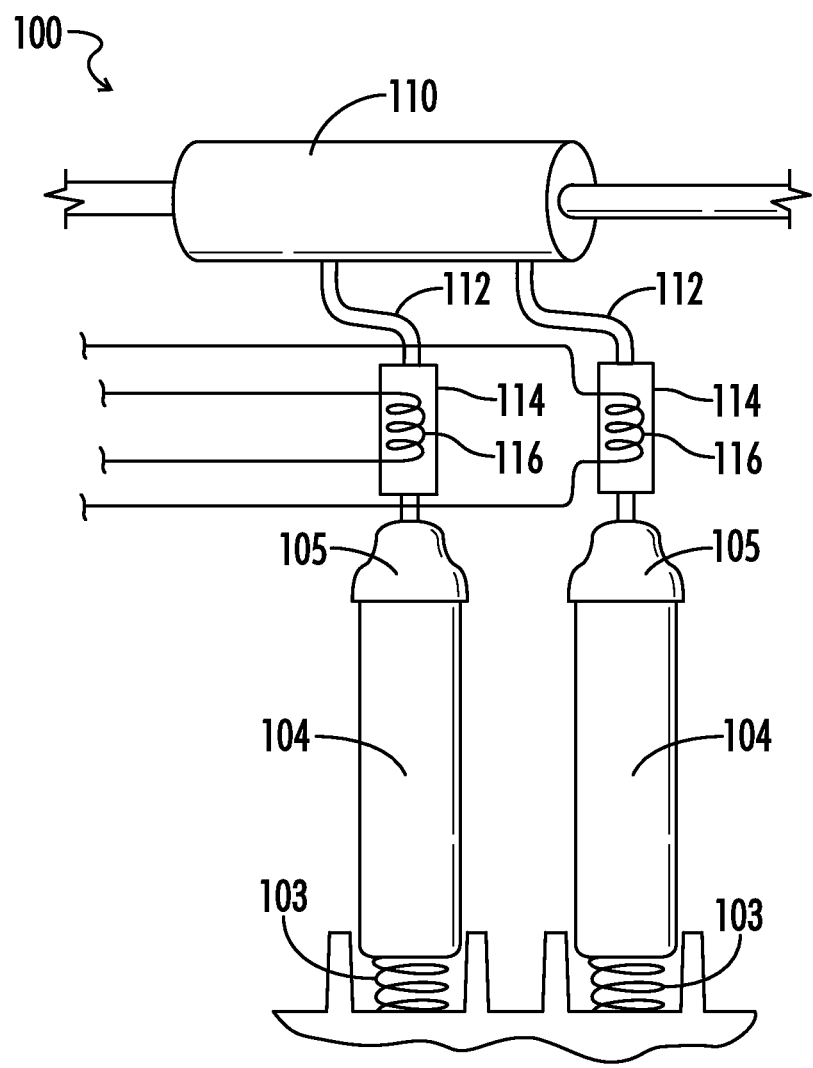
FIG. 4 is a simplified schematic of a supplemental fluid delivery system as shown in FIG. 3.

In various embodiments of apparatus 10, a supplemental fluid delivery system 100 allows one or more supplemental wound treatment fluids, such as hypochlorous acid, medications and disinfectants, to be introduced into the positive pressure fluid flow and delivered to the wound site through the wound dressing 6. Thus, as shown in FIGS. 3 and 4, the internal components of supplemental fluid delivery system 100 may include a fluid manifold 110 in fluid communication with wound treatment fluid output line 72. One or more supplemental fluid vials 104 may be coupled to manifold 110 through respective nozzles 105, controllable nozzle fittings 114, and supplemental fluid lines 112. In some embodiments, the vials 104 may be internally pressurized using a propellant or externally pressurized using springs 103 biased against a movable floor of vials 104.

In other embodiments not shown, external vials or containers of supplemental wound treatment fluids may be provided and supported on the exterior of housing 12 and fluidly coupled to the internal components of the supplemental fluid delivery system 100.

A solenoid 116 may be configured inside each nozzle fitting 114 and electrically coupled to controller 60. The controller is programmed or otherwise configured to actuate one or more solenoids 116, causing its respective nozzle fitting 114 to depress nozzle 105 of a corresponding vial 104. This selectively meters the supplemental wound treatment fluids contained in vials 104 into manifold 110.

When the therapeutic fluids stored in vials 104 are dispersed into manifold 10 during the positive pressure operational mode, the flow of oxygen or air from compressor pump 30 carries the therapeutic fluids to wound dressing 6. While supplemental fluid delivery system 100 is illustrated and described using a solenoid actuated nozzle fitting used in conjunction with pressurized fluid vials, other actuation mechanisms and fluid containers may be employed within the teachings of the present invention.

Controller 60 may programmed or otherwise configured to actuate supplemental fluid delivery system 100, so as to establish additional operational modes specific to desired fluid delivery wound treatment protocols. By way of example, wound treatment apparatus 10 may be configured via the user interface 18 and controller 60 to have an initial therapeutic operational mode, where a first vial 104 containing an antiseptic fluid, such as hypochlorous acid or a saline solution, is delivered through hermetically sealed wound dressing 6 to flush the wound site. In an embodiment, this first delivery of a therapeutic fluid may be followed by a second therapeutic operational mode, where a second vial 104 containing a medicine, such as an antibiotic, is delivered through wound dressing 6 to the sealed wound site. Delivering therapeutic fluids directly to the wound site through wound dressing 6 may eliminate or reduce the need to remove the wound dressing 6 to apply localized or topical fluid treatments.

One example of a wound treatment protocol that includes the use of hypochlorous acid as a supplemental wound treatment fluid may include the use of a hydrophobic wound dressing, such as a dressing described in U.S. Pat. No. 4,617,326 and available from Abigo Medical AB under the Sorbact®. The hypochlorous acid compound may contain various stabilizers and other compounds to achieve the desired therapeutic properties.

Oxygen Concentrator

In certain embodiments, oxygen concentrator 200 acts as an internal oxygen and fluid supply source. In a particular embodiment, oxygen concentrator 200 may be of a type developed by Separation Design Group, LLC of Waynesburg, Pa., e.g., a self-contained modular device having a replaceable screw-in sieve bed that, when powered by a small compressor, can output 30 ml/minute of oxygen at 92% purity. In one aspect, oxygen concentrator 200 may a small, light-weight device that provides oxygen-enriched air using an ultra-rapid adsorption cycle based on advanced molecular sieve materials. Such devices are disclosed in U.S. Patent Publication No. 20120192864, the entirety of which is incorporated herein by reference.

For example, the module for the oxygen concentrator 200 may include a cartridge having a feed end and a product end, an input port for incoming air flow in the feed end, a feed end plug, a diffusion channel in the feed end, and an adsorbent bed contained the cartridge. The adsorbent bed will include a molecular sieve material having an average particle size of about 60 .mu.m to 180 .mu.m and having a substantially spherical shape and an aspect ratio of length to diameter of less than about 6. A fibrous pad may be positioned at one or both ends of the adsorbent bed. The module includes an output port for an oxygen-enriched product flow in the product end. A product end plug includes gas flow controls and at least one collection channel. The module further may include an enriched-oxygen product tube having an input end plug with an oxygen input port in the end plug and an output end plug having an oxygen output port in the output end plug. A product end block includes a passageway for transport of oxygen-enriched product with the cartridge and the enriched-oxygen product tube being connected to the product end block.

Oxygen concentrator 200 provides a supplemental fluid flow of oxygen enriched air when the apparatus 10 is operating in the positive pressure operational mode. Oxygen concentrator 200 generally provides sufficient oxygen and fluid flow to eliminate the need for an external oxygen source. As shown in the embodiment of FIG. 3, a valve 202 connects oxygen concentrator 200 to oxygen source line 70. Concentrator 200 and valve 202 may both be electrically connected or otherwise operatively coupled to controller 60, which controls the operation of the concentrator 200 and actuates the valve 202 to introduce oxygen provided from the concentrator 202 into oxygen source line 70.

Self-Sterilization System

In certain embodiments, a self-sterilization system 300 allows sterilization of all internal lines and components of wound treatment apparatus 10. The self-sterilization system 300 may include a source of a sterilization fluid, e.g. an ozone generator (not shown) operatively connected to oxygen source line 70 by a sterilizing fluid valve 304. The ozone generator may be of a conventional design and particularly selected to be light in weight and to have small footprint. Self-sterilization system 300 may also include a conventional ozone accumulator connected to the ozone generator for storing a volume of ozone to be used in the sterilization process. The ozone generator and valve 304 may both be electrically connected or otherwise operatively coupled to controller 60, which controls the operation of the generator and actuates the valve 304 to introduce ozone into oxygen source line 70. When the apparatus 10 is operating in a sterilization mode, compressor pump 30 circulates the ozone through the various pumps, accumulators, lines, valves, and fittings of wound treatment apparatus 10, thereby killing pathogens and microbes in the apparatus. In some embodiments, the various lumens 80, 82, 84, 86 and 88 are disconnected from wound treatment apparatus 10, connector fitting 21 is closed, and connector fittings 23 and 25, as well as connector fittings 27 and 29 are looped together using short sections of lumen or specialized connector loops (not shown) to close the fluid flow system before the sterilization mode is initiated. Controller 60 may be programmed or otherwise configured via the user interface 18 to initiate the sterilization mode as desired and clinically appropriate.

Exudate Safety System

Figure 5:
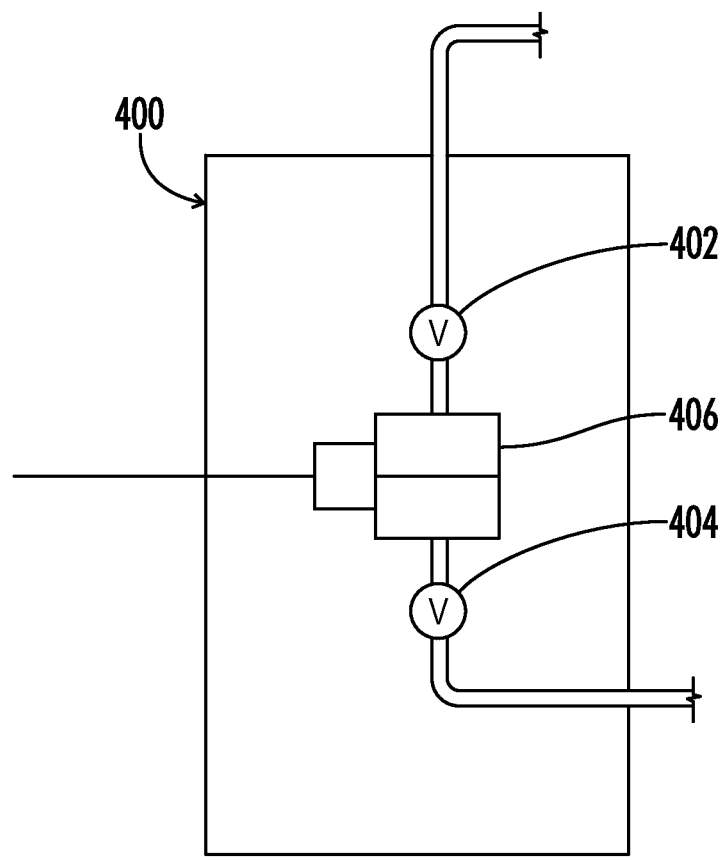
FIG. 5 is a simplified schematic of an embodiment of an exudate safety system.

In some embodiments of the apparatus 10, an exudate safety system 400 prevents exudate from contaminating wound treatment apparatus 10 by preventing exudate from entering and contaminating the apparatus. As shown in the embodiment of FIGS. 3 and 5, safety system 400 may include first and second pressure sensors or gauges 402 and 404 functionally coupled to a logic unit 406 that monitors pressure differentials between sensors 402 and 404. First sensor 402 senses a first device pressure, e.g. the pressure in wound treatment fluid output line 72. Second sensor 404 senses a second device pressure, e.g. the pressure in vacuum return line 74. Monitoring the pressure differential at these two (or other suitable) pressure sensing nodes can indicate that exudate may be from flowing back through wound dressing 6 and wound treatment fluid supply lumen 82 to contaminate portions of wound treatment apparatus 10.

In some embodiments, exudate safety system 400 may be functionally coupled to controller 60 so that alerts, alarms and interrupts can be triggered if an exudate contamination event cannot be inhibited or is detected. In other embodiments, controller 60 may be programmed or otherwise configured to respond to signals from logic unit 406. In response to these signals, and in particular in response to measured pressure differentials indicating a potential exudate contamination event, controller 60 can initiate adjustments at compressor pump 30, vacuum pump 40, and/or at one or more controllable apparatus valves to bring the sensed pressures back into a safe range to prevent contamination. In some embodiments, logic unit 406 may be integral with controller 60.

Blood Detection System

In various embodiments of apparatus 10, a blood detection system 500 may be provided to monitor blood content within the exudate drawn from the wound site. As shown in the embodiment of FIG. 3, blood detection system 500 may be connected in fluid communication with drainage loop line 76 and further electrically connected or otherwise operatively coupled to controller 60. Blood detection system 500 monitors exudate drawn from wound dressing 6 for blood to ensure that bleeding at the wound site is not exacerbated during negative pressure treatment. Blood detection system 500 may employ any variety of conventional methods and sensors for detecting the presence and level of blood in the exudate.

Figure 6:
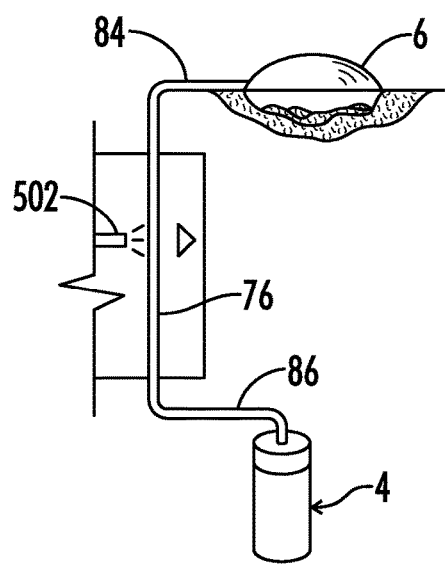
FIG. 6 is a simplified schematic of an embodiment of a blood detection system.
Figure 7:
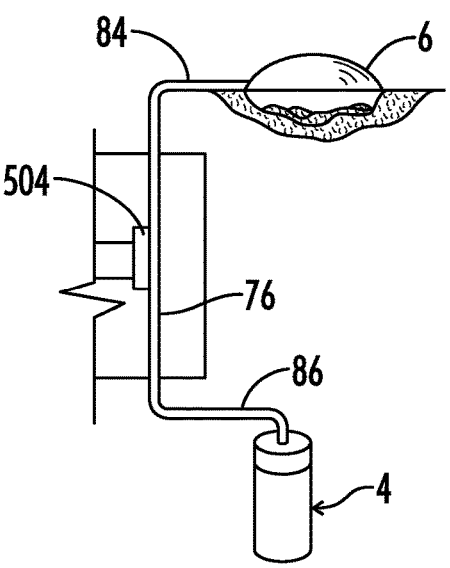
FIG. 7 is a simplified schematic of a second embodiment of a blood detection system.
Figure 8:
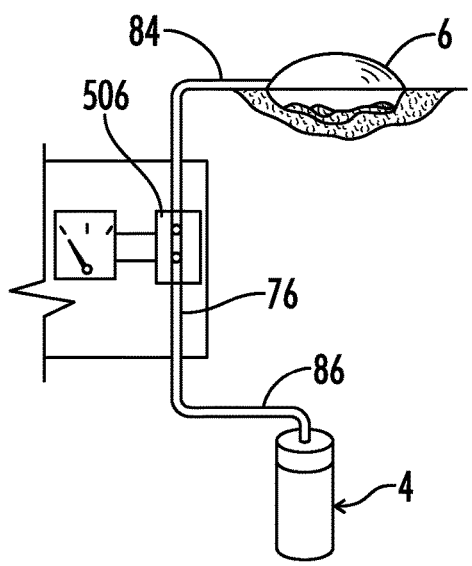
FIG. 8 is a simplified schematic of a third embodiment of a blood detection system.

Examples of blood detection sensors usable in blood detection system 500 are illustrated in FIGS. 6-8. In the embodiment of FIG. 6, blood detection system 500 may employ one or more optical sensors 502 and related circuitry to provide a spectral (light and/or color) analysis of the exudate to detect the presence of blood. In another embodiment as shown in FIG. 7, blood detection system 500 may use circuitry 504 to directly or indirectly measure the capacitance or other electrical property of the exudate in relation to that of blood. In yet another embodiment as shown in FIG. 8, the blood detection system 500 may use sensors and circuitry 506 to measure the pH of the exudate to detect blood in the exudate (FIG. 6).

In various embodiments not shown, blood detection system 500 may further include an alarm or other device responsive to the blood detection sensor 502, 504, or 506 to provide a visible or audible signal that blood has been detected in the exudate. Alternatively, or in addition, the blood detection system 500 may be functionally coupled to controller 60 so that a blood detection event can be determined and signaled to a user of the apparatus 10 via user interface 18.

Different embodiments of the apparatus 10 may be portable and may combine a positive pressure source, a negative pressure source, a controller, and various combinations of the oxygen concentrator, supplement fluid delivery system, exudate safety system, self-sterilization system, and/or blood detection system.

In some embodiments of the apparatus, the controller 60 may include (or be coupled to) program memory that stores configuration and operational data that define and automatically implement the various operational modes and/or different wound treatment protocols as described above. In some embodiments, commands may be entered at the user interface 18 that define or modify operational modes and/or wound treatment protocols.

The embodiments of the present invention herein described and illustrated are not intended to be exhaustive or to limit the invention to the precise form disclosed. They are presented to explain the invention so that others skilled in the art might utilize its teachings. The embodiment of the present invention may be modified within the scope of the following claims.

What is claimed is:

1. A wound treatment apparatus comprising:
a housing;
a positive pressure device comprising a compressor pump disposed within the housing and configured for fluid coupling to an external fluid source and to an external wound dressing, the positive pressure device effective to deliver therapeutically effective levels of a primary wound treatment fluid under positive pressure to a the external wound dressing during a first wound treatment mode;
a negative pressure device comprising a vacuum pump disposed within the housing and configured for fluid coupling to the external wound dressing, the negative pressure device effective to provide therapeutically effective levels of a negative pressure to the external wound dressing during a second wound treatment mode;
an oxygen concentrator disposed within the housing and operatively coupled to the compressor pump, the oxygen concentrator effective to supply oxygen enriched air to the compressor pump;
a controller disposed within the housing and operatively connected to the positive pressure device and to the negative pressure device;
an oxygen accumulator valve operatively coupled to the controller;
a vacuum accumulator valve operatively coupled to the controller;
an oxygen accumulator fluidly coupled to the compressor pump via the oxygen accumulator valve; and
a vacuum accumulator fluidly coupled to the vacuum pump via the vacuum accumulator valve,
wherein the controller is configured to selectively switch the apparatus between the first wound treatment mode and the second wound treatment mode, and
wherein the controller is further configured to selectively actuate the oxygen and vacuum accumulator valves to facilitate application of positive and negative pressures at the external wound dressing when the apparatus is transitioning between the first and second wound treatment modes.

2. The apparatus of claim 1 further comprising:
a wound treatment fluid output line fluidly coupled to the positive pressure device, the wound treatment fluid output line configured to fluidly couple the positive pressure device to the external wound dressing;

a supplemental fluid delivery system disposed within the housing, the supplemental fluid delivery system operatively coupled to the controller and fluidly coupled to the wound treatment fluid output line; wherein the supplemental fluid delivery system comprises at least one supplemental fluid vial adapted to contain a supplemental wound treatment fluid; and the controller is further configured to cause the supplemental fluid delivery system to introduce a supplemental wound treatment fluid from the at least one supplemental fluid vial into the wound treatment fluid output line during the first wound treatment mode.

3. The apparatus of claim 1 further comprising:
a self-sterilization system disposed within the housing, the self-sterilization system comprising:
a sterilizing fluid valve operatively coupled to the controller; and
a source of sterilizing fluid fluidly coupled to the positive and negative pressure devices via the sterilizing fluid valve;
wherein, the controller is further configured to cause the self-sterilization system to selectively circulate sterilizing fluid through the positive pressure device and through the negative pressure device during a self-sterilization mode.

4. The apparatus of claim 3 wherein the source of sterilizing fluid comprises an ozone generator.

5. The apparatus of claim 1 further comprising:
a wound treatment fluid output line fluidly coupled to the positive pressure device, the wound treatment fluid output line configured to couple the positive pressure device to the external wound dressing;
a vacuum return line fluidly coupled to the negative pressure device and configured to couple the negative pressure device to an exudate container;
a negative pressure wound treatment fluid fitting configured to fluidly couple the negative pressure device to the external wound dressing;
a drainage loop line disposed within the housing, the drainage loop line fluidly coupled to the negative pressure wound treatment fluid fitting and configured to fluidly couple the negative pressure wound treatment fluid fitting to the exudate container; and
an exudate safety system disposed within the housing, the exudate safety system fluidly coupled to the vacuum return line and to the wound treatment fluid output line, the exudate safety system comprising:
a logic unit,
a first pressure sensor operatively coupled to the logic unit and fluidly coupled to measure fluid pressures inside the wound treatment fluid output line,
a second pressure sensor operatively coupled to the logic unit and fluidly coupled to measure fluid pressures inside the vacuum return line,
wherein the logic unit is responsive to the first and second pressure sensors and is configured to inhibit, determine and/or indicate an exudate contamination event by comparing fluid pressures inside the wound treatment fluid output line and the vacuum return line.

6. The apparatus of claim 5 further comprising a side pocket affixed to the housing, the side pocket configured to hold the exudate container.

7. The apparatus of claim 5 further comprising a blood detection system disposed within the housing and fluidly coupled to the drainage loop line, the blood detection system comprising at least one blood detection sensor functional to detect blood in exudate drawn from the external wound dressing during the second wound treatment mode.

8. A wound treatment apparatus comprising:
a housing;
a compressor pump disposed within the housing and configured for coupling to an external oxygen source and to an external wound dressing, the compressor pump further configured to deliver therapeutically effective levels of hyperbaric oxygen to the external wound dressing during a positive pressure operational mode;
a vacuum pump disposed within the housing and configured for coupling to the external wound dressing, the vacuum pump further configured to deliver therapeutically effective levels of negative pressure to a the external wound dressing during a negative pressure operational mode;
an oxygen concentrator disposed within the housing and operatively coupled to the compressor pump, the oxygen concentrator effective to supply oxygen enriched air to the compressor pump during the positive pressure operational mode;
a controller disposed within the housing and operatively connected to the compressor pump, to the vacuum pump, and to the oxygen concentrator;
a user interface functionally coupled to the controller;
an oxygen accumulator valve operatively coupled to the controller;
a vacuum accumulator valve operatively coupled to the controller;
an oxygen accumulator fluidly coupled to the compressor pump via the oxygen accumulator valve; and
a vacuum accumulator fluidly coupled to the vacuum pump via the vacuum accumulator valve,
wherein the controller is responsive to commands entered at the user interface and is configured to selectively switch the apparatus between the positive pressure and negative pressure operational modes, and
wherein the controller is further configured to selectively actuate the oxygen and vacuum accumulator valves to expedite application of positive and negative pressures at the external wound dressing during a transition mode between the positive and negative pressure operational modes.

9. The apparatus of claim 8, further comprising:
a supplemental fluid delivery system at least partially disposed within the housing, the supplemental fluid delivery system operatively coupled to the controller;
wherein the controller is further configured to cause the supplemental fluid delivery system to deliver a supplemental fluid to the external wound dressing during the positive pressure operational mode.

10. The apparatus of claim 9 wherein the supplemental fluid delivery system is configured to store and deliver hypochlorous acid as the supplemental wound treatment fluid.

11. The apparatus of claim 8 further comprising:
an ozone generator disposed within the housing,
wherein the controller is further configured to cause the ozone generator to deliver ozone to the compressor pump and to the vacuum pump during a self-sterilization mode.

12. The apparatus of claim 8 further comprising an exudate safety device disposed within the housing, the exudate safety device configured to:

sense operational fluid pressures associated with operation of the compressor pump and the vacuum pump, and inhibit or indicate exudate contamination of the apparatus by comparing the operational fluid pressures inside a wound treatment fluid output line and a vacuum return line.

13. The apparatus of claim 8 further comprising a blood detection sensor disposed within the housing, the blood detection sensor effective to detect blood in exudate drawn to the apparatus from a the external wound dressing during the negative pressure operational mode.

14. A portable wound treatment device comprising:
a housing comprising an exterior wall enclosing a device interior, and a user interface panel arranged in the exterior wall;
an oxygen supply connector panel coupled to the exterior wall and including at least one oxygen supply fitting extending through the exterior wall, the oxygen supply fitting configured to couple oxygen provided by an external oxygen source into the device interior;
a wound treatment connector panel coupled to the exterior wall and including a positive pressure fitting and a negative pressure fitting, the positive pressure fitting configured to couple oxygen under positive pressure from the device interior to an external wound dressing, and the negative pressure fitting configured to apply a negative pressure from the device to the external wound dressing and to extract wound exudate from the external wound dressing into the device;
a wound exudate connector panel coupled to the exterior wall and including a positive exudate fitting and a negative exudate fitting extending through the exterior wall, the positive exudate fitting configured to couple wound exudate from the negative pressure fitting to an exudate container, and the negative exudate fitting configured to provide a negative pressure to an exudate container;
a positive pressure pump disposed in the device interior and coupled to the positive pressure fitting, the positive pressure pump effective to provide oxygen under positive pressure to the positive pressure fitting during a hyperbaric oxygen treatment mode;
a negative pressure pump disposed in the device interior and coupled to the negative pressure fitting and to the negative exudate fitting, the negative pressure pump effective to provide negative pressure to the negative pressure fitting and to the negative exudate fitting during a negative pressure treatment mode;
an oxygen concentrator disposed in the device interior and operatively coupled to the positive pressure pump, the oxygen concentrator effective to supply oxygen enriched air to the positive pressure pump during the hyperbaric oxygen treatment mode; and a controller disposed in the device interior;
an oxygen accumulator system fluidly coupled to the positive pressure pump and operatively coupled to the controller;
a vacuum accumulator system fluidly coupled to the negative pressure pump and operatively coupled to the controller, wherein the controller is functionally coupled to the user interface panel, to the positive pressure pump, and to the negative pressure pump, the controller configured to activate the positive pressure pump and the oxygen concentrator during the hyperbaric oxygen treatment mode, and to activate the negative pressure pump during the negative pressure treatment mode, and wherein the controller is further configured to selectively actuate the oxygen and vacuum accumulator systems to facilitate application of positive and negative pressures at the external wound dressing during a device transition mode between the hyperbaric oxygen treatment mode and the negative pressure treatment mode.

15. The portable wound treatment device of claim 14 further comprising:
a supplemental fluid delivery system disposed within the device interior, the supplemental fluid delivery system operatively coupled to the controller and comprising a manifold configured to receive a supplemental wound treatment fluid and to deliver the supplemental wound treatment fluid to the positive pressure fitting; and
the controller is further configured to cause the supplemental fluid delivery system to deliver the supplemental wound treatment fluid to the positive pressure fitting during the hyperbaric oxygen treatment mode.

16. The portable wound treatment device of claim 15 further comprising:
a self- sterilization system disposed within the device interior, the self-sterilization system operatively coupled to the controller and configured to receive a sterilizing fluid and to deliver the sterilizing fluid to the positive and negative pressure pumps; and
the controller is further configured to cause the self-sterilization system to circulate the sterilizing fluid through the positive pressure pump and through the negative pressure pump during one or more device self-sterilization modes.

17. The portable wound treatment device of claim 16 further comprising:
an exudate safety system disposed within the device interior, the exudate safety system comprising a logic unit, a first pressure sensor operatively coupled to the logic unit and configured to sense a first device pressure, and a second pressure sensor operatively coupled to the logic unit and configured to sense a second device pressure; and
the logic unit is responsive to the first and second pressure sensors and is effective to inhibit or signal an exudate contamination event by comparing the first and second device pressures.

18. The portable wound treatment device of claim 17 further comprising:
a carrying handle attached to the exterior wall; and
a blood detection system disposed in the device interior and comprising a blood detection sensor functional to detect blood in wound exudate drawn from the external wound dressing during at least the negative pressure treatment mode.

* * * * *